United States Patent
Christensen et al.

(10) Patent No.: US 7,022,107 B1
(45) Date of Patent: Apr. 4, 2006

(54) INFUSION PUMP WITH PRESSURE REGULATOR

(75) Inventors: James Christensen, Glendora, CA (US); John Krug, Orange, CA (US)

(73) Assignee: Advanced Infusion, Inc., Tempe, AZ (US)

( * ) Notice: Subject to any disclaimer, the term of this patent is extended or adjusted under 35 U.S.C. 154(b) by 0 days.

(21) Appl. No.: 09/670,735

(22) Filed: Sep. 27, 2000

Related U.S. Application Data

(63) Continuation-in-part of application No. 09/400,579, filed on Sep. 22, 1999.

(51) Int. Cl.
*A61M 37/00* (2006.01)

(52) U.S. Cl. .................................... 604/141; 604/891.1

(58) Field of Classification Search ............ 604/890.1, 604/891.1, 151, 153, 154, 131, 132–135, 604/150, 152, 141, 892.1
See application file for complete search history.

(56) References Cited

U.S. PATENT DOCUMENTS

| | | | |
|---|---|---|---|
| 3,731,681 A | 5/1973 | Blackshear et al. ......... 128/214 |
| 3,993,069 A | 11/1976 | Buckles et al. .......... 128/214 F |
| 4,106,510 A | 8/1978 | Hakim et al. ................ 128/350 |
| 4,299,220 A | 11/1981 | Dorman ....................... 128/260 |
| 4,714,462 A * | 12/1987 | DiDomenico ................. 604/67 |
| 4,718,893 A | 1/1988 | Dorman et al. ................ 604/67 |
| 4,772,263 A | 9/1988 | Dorman et al. ............. 604/132 |
| 5,061,242 A | 10/1991 | Sampson .................... 604/118 |
| 5,067,943 A | 11/1991 | Burke ......................... 604/141 |
| 5,080,652 A | 1/1992 | Sancoff et al. .............. 604/132 |
| 5,088,983 A | 2/1992 | Burke ......................... 604/141 |
| 5,242,406 A | 9/1993 | Gross et al. ................. 604/132 |

* cited by examiner

*Primary Examiner*—Kevin C. Simmons
(74) *Attorney, Agent, or Firm*—Koppel, Jacobs, Patrick & Heybl; Michael J. Ram

(57) ABSTRACT

An infusion pump for infusing drugs or other fluids into the body. The pump consists of two chambers. The storage chamber holds a large volume of drug at a variable and elevated pressure, which exceeds the preselected outflow pressure. The outflow chamber holds a smaller volume of drug at a constant outflow pressure. A moveable diaphragm attached to a valve controls the entry of the drug from the storage chamber into the outflow chamber. The pressure of the drug in the outflow chamber is determined by the forces applied to the diaphragm. The drug from the outflow chamber flows through a flow restrictor and catheter into the patient at a constant flow rate.

7 Claims, 3 Drawing Sheets

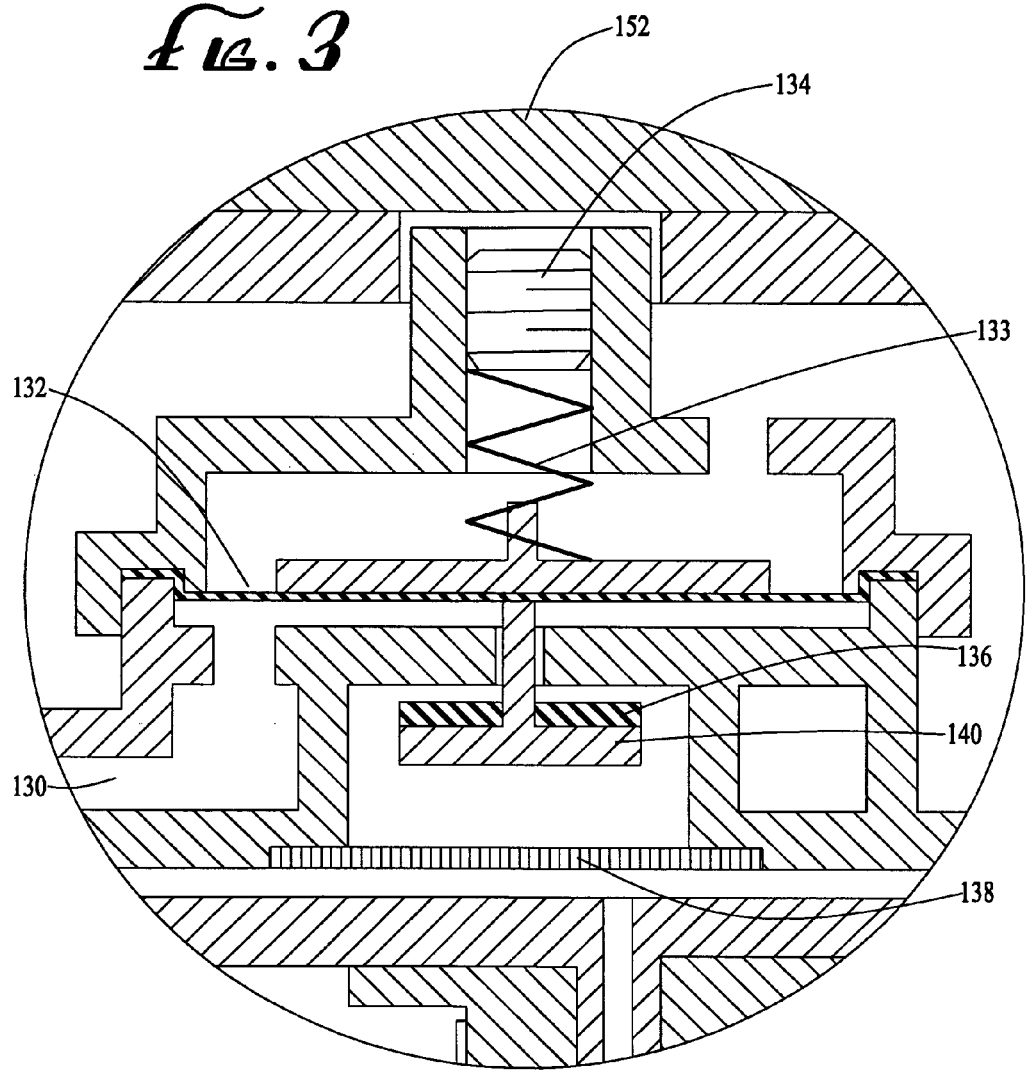

INFUSION PUMP WITH PRESSURE REGULATOR

This is a continuation-in-part of U.S. patent application Ser. No. 09/400,579 filed Sep. 22, 1999. The present invention generally relates to a liquid dispensing device, and more particularly, to an infusion pump having a pressure regulator for delivering fluid from the infusion pump at a constant pressure.

A number of prior publications describe methods for regulating the pressure of a fluid delivered from a drug infusion pump incorporating a flow restrictor. Regulation of the fluid pressure is necessary since the flow rate through a flow restrictor of a drug delivered to a patient is directly proportional to the pressure of the fluid across the restrictor. Depending on the method used to pressurize the fluid within a drug infusion pump, various methods have been employed to provide a uniform delivery pressure from the pump. U.S. Pat. No. 3,993,069 to Buckles, et al, discusses an improvement in making elastomeric bladders for liquid dispensers. The bladders are inflated by filling with the liquid to be delivered. By refining the formulation of the polyisoprene elastomer used to form the bladder which pressurizes the fluid, and by controlling the deflated and inflated geometries of the bladder, they are able to achieve a pressure constant to within ±10% during discharge of about 90% of the bladder contents. Any deviation to either the formulation or geometry would result in a greater pressure variation. The outer configuration of this pump is generally restricted to the configuration of the freely inflated bladder (sausage shaped).

Although a ±10% pressure variation is acceptable for some applications, when it is combined with the variation occurring from other components of the infusion pump, in particular the flow restrictor, the overall flow rate variation can approach unacceptable levels. In addition, the restrictions on the geometry of the bladder in order to achieve uniform pressure, severely limits the design of the drug infusion pump.

U.S. Pat. No. 5,080,652 to Suncoff, et al, discusses another methodology to achieve a relatively uniform delivery pressure. Multiple elastic membranes are used which expand into a spherical configuration to maintain relatively constant pressure on the liquid contained within. Although this design may achieve a relatively uniform pressure over a portion of the expansion range, there are still areas of significant pressure variation especially during the first portion of the inflation. Furthermore, there is a significant variation in the pressure achieved inside all elastomeric chambers over time as the elastomeric material stress relaxes. Within hours the pressure can degrade in elastic chambers made of latex, isoprene, silicone, and other elastomeric materials. This pressure relaxation can approach 50% in elastomeric chambers that are inflated for a day. Since liquids are pressurized in these chambers for periods greater than a day the pressure decay over time becomes significant.

Springs have also been used to pressurize the drug contained within an infusion pump. U.S. Pat. No. 4,772,263 to Dorman, et al, discusses the use of a flexible spring diaphragm to pressurize the fluid contained within the pump. By properly selecting the segments of the spring diaphragm a relatively constant pressure can be obtained for a portion of the volume delivered from the pump. However, there are significant portions of the pump volume that are delivered at either a higher or lower pressure as shown in the force versus deflection curve for this pump contained in their patent.

U.S. Pat. No. 5,346,476 to Elson is another example of a spring driven plunger applied to a fluid filled bladder. This patent attempts to maintain the delivery pressure constant by using springs having a change of force over their expansion range.

Again, the above prior art suffers from the disadvantage that the external geometry of the pump is constrained to the geometry of the spring diaphragm. Since this geometry is usually round, pumps produced using this means of pressurization are shaped like hockey pucks. Further, the volume of these pumps is usually limited to small volumes since the deflection of the spring diaphragm is limited to small movements. As the volume of the pump becomes greater the volume of the fluid delivered at a non-constant pressure becomes greater.

There are other methods for pressurizing a fluid contained within a pump where the design is not constrained by geometry. One of these methods is exemplified by U.S. Pat. No. 3,731,681 to Blackshear, et al, as well as similar patents, which discloses an infusion pump that uses a liquid/vapor equilibrium to maintain a constant pressure on the fluid contained within the pump. The equilibrium condition for the liquid/vapor equilibrium in these pumps is extremely sensitive to temperature and pressure changes. For example, the pressure on the fluid contained in the pump changes approximately 0.5 psi for each degree Fahrenheit change. Assuming an 8 psi delivery pressure, a 25% increase in pressure would be obtained by a temperature increase of 4° F.

The above, and similar, prior art all try to control the delivery pressure of the fluid pump by controlling the fluid pressurizing means. This generally is not effective in producing a constant delivery pressure over the entire outflow volume of these pumps. A more effective means would be to control the pressure inside the pump directly.

U.S. Pat. No. 4,718,893 to Dorman, et al, discusses the use of a pressure regulator to maintain the liquid held within the drug pump at a constant pressure. The pressure regulator consists of an expansible chamber, which changes volume based on the pressure within the drug chamber so as to maintain the entire volume of drug in the pump at a constant pressure. This concept works for small volume drug pumps where the pressure prior to regulation is near constant. However, it is impractical for large volume pumps where significant pressure changes are involved as the volume inside the pump varies from filled to near empty.

In order to overcome the need to maintain a constant pressure on the bulk of the fluid contained within an infusion device, it would be desirable to have a pressure regulator that maintains the fluid delivered from the infusion pump at a constant pressure. Such a pressure regulator would allow the fluid contained within the infusion device to be pressurized by any means, to be maintained at any pressure greater than the delivery pressure, and would free the constraints on device geometry.

SUMMARY OF THE INVENTION

The present invention relates to an apparatus and method for controlling the pressure of a drug or fluid in the outflow chamber of a drug infusion pump.

The preferred embodiment of the present invention consists of an infusion pump comprised of two chambers. The first chamber is a storage chamber, which can hold a large volume of fluid under pressure. This pressure in the first chamber can be highly variable as long as it exceeds the required outflow pressure from the pump. Also, various different means can be used to generate the pressure on the fluid in the first chamber. The second chamber, which incorporates a flexible diaphragm attached to a valve, contains fluid delivered from the first chamber. The second chamber is maintained at a preset constant pressure. The pressure in the second chamber is determined by the area of the diaphragm and the external spring force applied to it. Fluid from the second chamber is infused into the patient through a flow restrictor which controls the rate of infusion.

Accordingly, the current invention provides a new and improved infusion device for dispensing fluids and medications to a patient, provides a new and improved means for maintaining the pressure of the fluid delivered from the infusion device at a constant pressure, provides a new and improved infusion device for delivering a fluid at constant pressure where the geometry and pressurizing means is not constrained by the geometry of the device, and provides a new and improved pressure regulator for an infusion device whose pressure can be adjusted to a pre-selected value.

In accordance with these and many other objects of the current invention, a pressure regulator placed between the pressurized fluid storage chamber and the outflow chamber of the infusion device will maintain the pressure of the fluid in the outflow chamber at a constant pressure.

BRIEF DESCRIPTION OF THE DRAWINGS

The preset invention, together with the above and other objects and advantages, can best be understood from the following detailed description of the embodiment of the invention illustrated in the drawings, wherein:

FIG. 3 is an enlarged cross section of the circled portion of FIG. 2.

DETAILED DESCRIPTION

Figure 1:
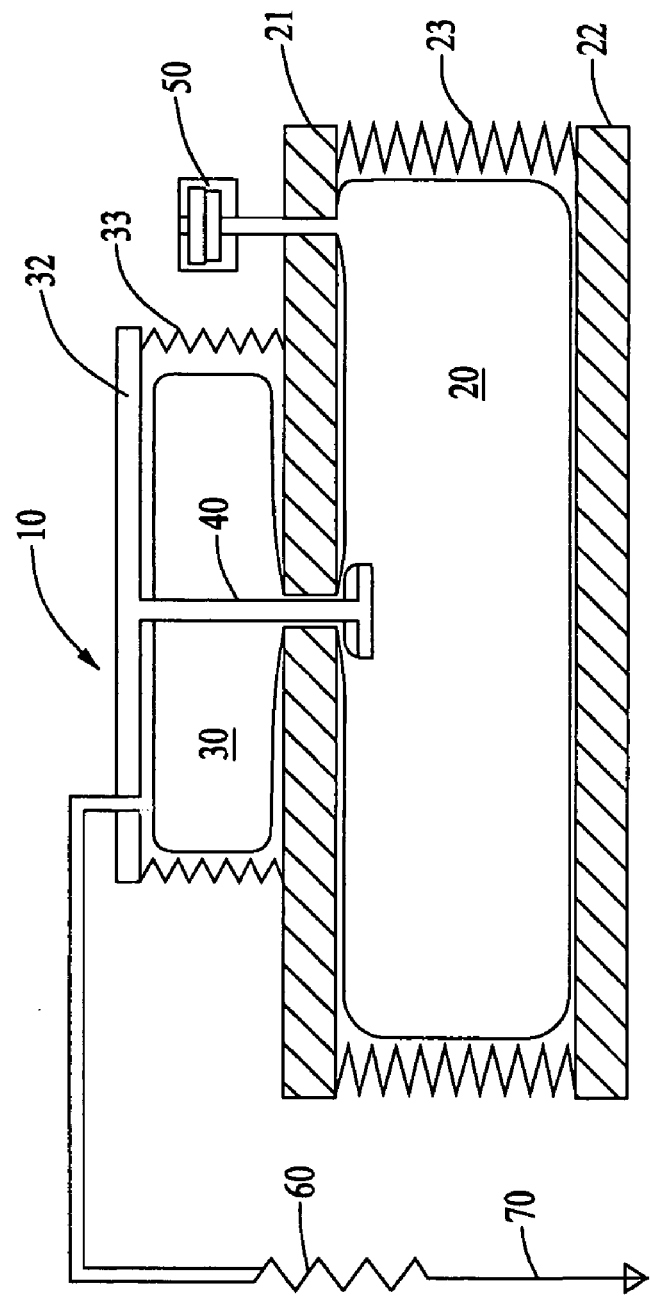
FIG. 1 is a schematic cross-sectional view of a general representation of a first embodiment of the present invention having a storage chamber, a pressure regulator, and an outflow chamber.

FIG. 1 shows a general representation of an infusion pump incorporating features of the present invention. The infusion pump 10 includes a variable volume and pressure storage chamber 20 and an outflow chamber 30. The storage chamber 20 is located between wall 21 and a moveable diaphragm or base 22. The wall 21 and diaphragm 22 are interconnected by a spring arrangement 23. The spring arrangement 23 functions as a force producing device causing the diaphragm 22 to exert a variable force on a drug solution in the storage chamber 20. It will be appreciated that any other number of force producing devices, such as gas filled cylinders, spring driven pistons or rolling diaphragms, or elastomeric chambers, where spring arrangement 23 represents the stretch of the elastomeric chamber, might be used to exert a force on the drug solution.

In the representation shown, the outflow chamber 30 shares the wall structure 21 with the pressure storage chamber, the wall 21 being located between the two chambers. The outflow chamber has a separate diaphragm 32, and a spring arrangement 33. The outflow chamber 30 of the infusion pump 10 is interconnected to the storage chamber 20 by a valve arrangement 40 which controls the fluid flow into the outflow chamber 30. The spring arrangement 33 functions as a force producing device causing the diaphragm 32 to exert a preselected force on the drug solution in the outflow chamber 30. When the pressure in the outflow chamber 30 falls below the preselected pressure, the force exerted on the diaphragm 32 by the fluid in the outflow chamber 30 drops below the force produced by the spring arrangement 33 and the valve arrangement 40 opens which allows high pressure fluid from the storage chamber 20 to enter the outflow chamber 30. When the pressure in the outflow chamber 30 is the same as, or slightly exceeds, the preselected pressure, the force exerted on the diaphragm 32 by the fluid in the outflow chamber 30 is greater than the force produced by the spring arrangement 33 and closes the valve arrangement 40.

The pressure regulator shown is capable of regulating the pressure in the outflow chamber to ±5%. Typical outflow pressures selected for infusion devices range from about 1 psi to over 10 psi. Pressures in the storage chamber can range over 20 psi in some infusion devices.

The storage chamber 20 of the infusion pump 10 is filled with fluid which is passed through the one-way check valve 50. The volume of fluid contained in the storage chamber 20 will vary from a large volume, when filled, to empty as the contents of the infusion pump 10 are dosed to the patient. The pressure inside the storage chamber 20 may be highly variable depending on the force producing device selected to pressurize the storage chamber 20.

The valve arrangement 40 will provide a steady, regulated flow of fluid from the storage chamber 20 into the outflow chamber 30. As fluid is administered from the outflow chamber 30 to the patient, the pressure of the fluid in the outflow chamber 30 drops below the preselected outflow pressure, the valve arrangement 40 opens and allows fluid from the storage chamber 20, which is at a higher pressure than the preselected outflow pressure, to flow into the outflow chamber 30. When the pressure in the outflow chamber 30 reaches the preselected outflow pressure once again, the valve arrangement 40 closes. The volume of fluid contained in the outflow chamber 30 will usually be very small and the movement of the diaphragm 32 will be very little.

Fluid from the outflow chamber 30 is infused into the patient through a flow restrictor 60 and catheter 70 which are attached to the top 12 of the infusion pump 10 and control the flow rate of the fluid.

A preferred arrangement for the catheter and flow restrictor, as described in U.S. patent application Ser. No. 09/400,579 filed Sep. 22, 1999, is a catheter tube with a flow restrictor portion located within a section of the catheter tube such that the flow rate can be adjusted by trimming the length of the flow restrictor portion and surrounding catheter tube assembly. The tubing can be trimmed at the time of manufacture or can be trimmed at a later time, such as when connected to the fluid delivery pump.

The flow restrictor tubing can be any flexible micro-bore tubing that can be easily trimmed without distorting the trimmed end. The flow restrictor tubing is positioned within the lumen of the catheter tubing so that no fluid will flow between the outside of the flow restrictor tubing and the wall of the lumen of the catheter tubing. In the device shown the catheter is attached to the infusion device after trimming by means of a hollow needle on the end of the tubing, the needle being used to pierce a rubber septum located in the wall of the flow chamber 30. However, one skilled in the art will recognize that various different attachment means, such as a Touhy-Borst or luer lock fitting can be used.

As the catheter flow restrictor assembly is shortened by trimming, the flow rate will increase in linear proportion to the initial length of the flow restrictor tubing. For example, if the length of the flow restrictor tubing is cut in half, the flow rate will double.

The dimensions of the flow restrictor tube can be determined from Poiseuille's Law as expressed in the equation:

$$Q = \frac{Pr^4}{8Ln}$$

where Q is the flow rate in cc/sec, P is the pressure drop through the tube in dynes/cm, r is the internal radius of the tube in cm, L is the length of the tube in cm, and n is the viscosity in poise of the fluid flowing through to tube. From this equation it can be seen that flow rate is inversely related to the length of the flow restrictor tube. For example, if the tube length is cut in half, the flow rate doubles. It can also be seen that the flow rate is related to the fourth power of the radius. A small change in the internal diameter of the flow restrictor tube can have a major change on the flow rate. For example, if the internal diameter is increased from 0.0020" diameter to 0.0024" the flow rate will more than double. From this relationship, a suitable flow restrictor tube can be chosen which will provide the desired flow rates and allow accurate trimming to alter the flow rate but not be overly long so that the cost of the device is significantly increased.

As an example, several catheter and flow restrictor tube assemblies were constructed from 65D durometer polyurethane catheter tubing having an ID of 0.020 inch, an OD of 0.030 inch, and a length ranging from 24 to 48 inches. Polyimide tubing of several internal diameters and lengths were assembled into the polyurethane catheter tubing using a cyanoacrylate adhesive. The catheter and flow restrictor tube assemblies were connected to an infusion device operating at a pressure of 6 psi. The flow rate through the catheter and flow restrictor tube assembly is given in the chart below:

TABLE I

Flow Restrictor Tube Length (inch) to Obtain Selected Flow Rate at 6 psi

| ID | 0.5 ml/hr | 1.0 ml/hr | 2.0 ml/hr | 4.0 ml/hr |
| --- | --- | --- | --- | --- |
| 0.0031" | 8.80 | 4.40 | 2.20 | 1.101 |
| 0.0028" | 5.85 | 2.93 | 1.47 | 0.74 |
| 0.0025" | 3.70 | 1.86 | 0.93 | 0.47 |
| 0.0022" | 2.22 | 1.11 | 0.56 | 0.28 |

Typical wall thicknesses of the polyimide inner tube are 0.0003 to 0.0005 resulting in outer diameters from about 0.0028 to about 0.0041. It is possible that minor variances in the internal diameter of the flow restrictor tube will occur due to manufacturing inaccuracies. These variances can cause a large variation in the flow rate through the restrictor tube since flow rate varies as the fourth power of the diameter. Therefore, as part of the construction of the catheter and flow restrictor tube assemblies, the actual flow rate of the assembly can be measured and the catheter and flow restrictor tube assembly trimmed to obtain a more accurate initial flow rate. A calibration curve for trimming the catheter to adjust flow rates is the established for each particular catheter/flow restrictor assembly. In this way precise flow rate assemblies can be manufactured.

Figure 2:
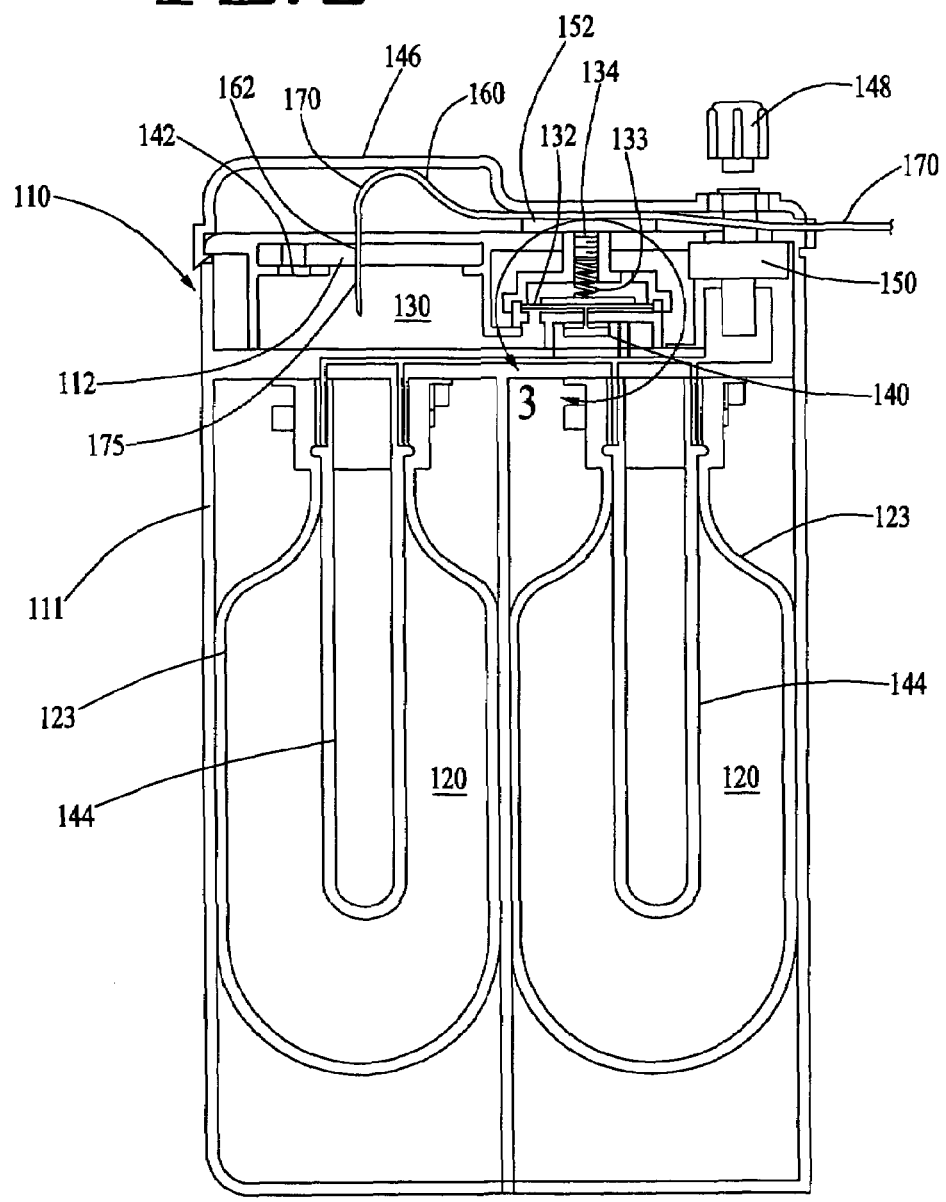
FIG. 2 is a cross-sectional view of a second embodiment of the present invention also having a storage chamber, pressure regulator, and outflow chamber.
Figure 1:
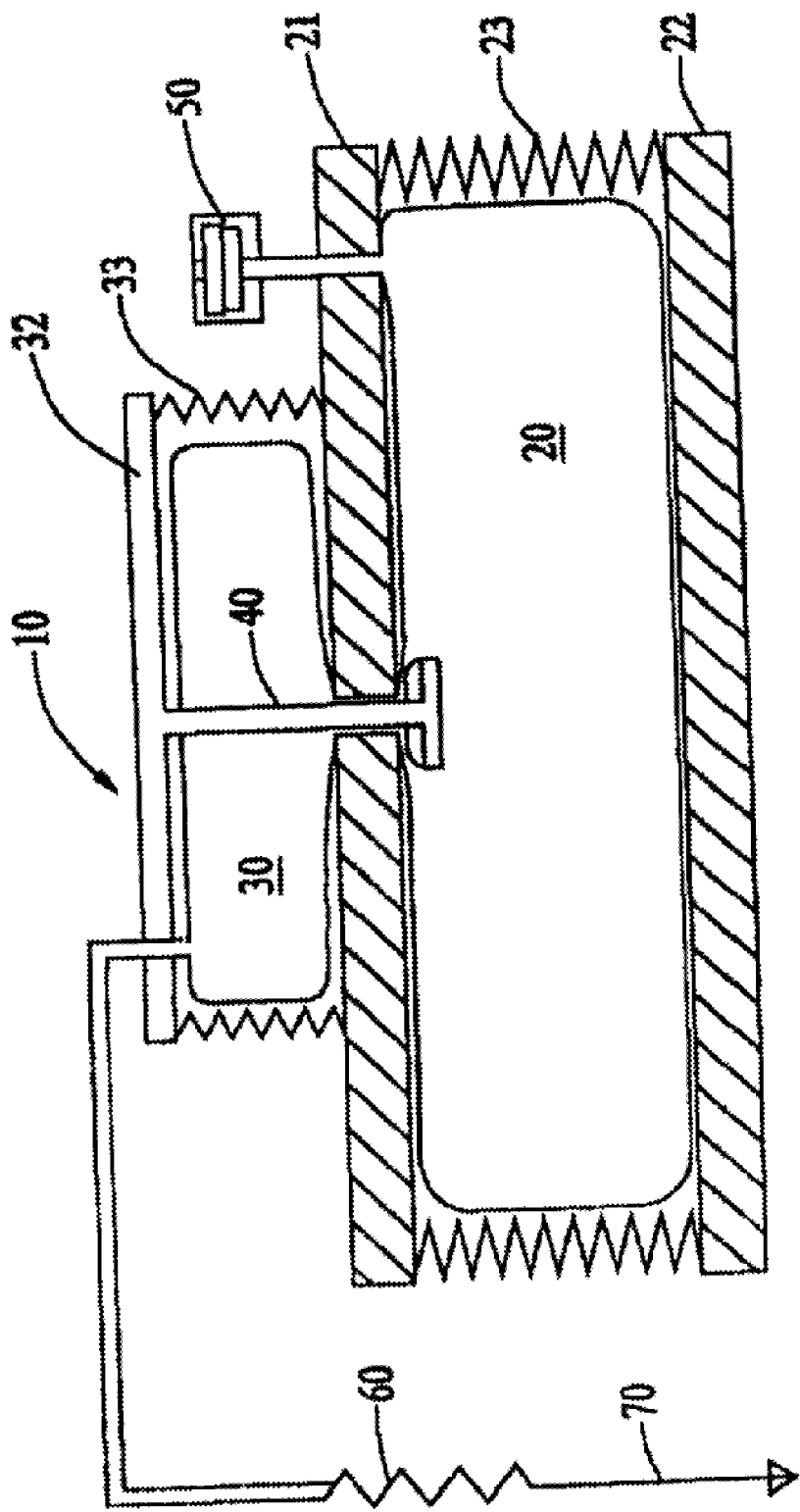

The flow rate of a fluid through a flow restricting device is dependent on the pressure drop across the flow restricting device. By maintaining a constant pressure in the outflow chamber of the pump, the amount of drug administered to the patient will be constant. As shown in the embodiment of FIG. 2, a catheter assembly 170, including a flow restrictor tube 160 with a needle 162 attached to the end of the catheter using a cyanoacrylate adhesive filler material, is utilized. The flow rate of the flow restrictor tube 170 had been measured and calibrated using flowing water at 6.0 psi. The actual flow rate was then determined, and the length of restrictor tube was cut to obtained the desired flow rate. After the flow restrictor tubing had been trimmed, a polyurethane catheter was placed over the flow restrictor tube and sealed to the needle using cyanoacrylate adhesive to form the catheter assembly 170. While particular types of flow restrictors are described, it will be appreciated that other styles of fluid delivery devices might be attached to the infusion pump to administer the drug solution to the patient.

FIG. 2 is a cross-sectional view of an operable prototype of the present invention. FIG. 3 is an enlarged cross-sectional view of the pressure regulator components at the junction between the fluid storage chamber and the outflow chamber. Infusion pump 110 includes a variable volume and pressure storage chamber 120 formed by two elastomeric bladders 123. As fluid is placed into the infusion pump 110 through a one-way check valve 150, the elastomeric bladder 123 expand to hold the fluid and maintain it under pressure. The elastomeric bladders 123 will expand until they fill the volume inside the outer shell 111 of the infusion pump 110. In the preferred embodiment shown the volume of fluid held in the storage chamber is about 200 ml. However, typical devices hold from about 50 ml to over 500 ml of fluid. The outflow chamber holds about 2 ml to about 10 ml of fluid. The pressure applied to the fluid in the storage chamber by the elastomeric bladders typically range from about 6 psi to 25 psi. This pressure is selected so that, as a minimum, it exceeds the desired pressure of the outflow chamber 130, discussed below.

Fluid held in the storage chambers 120 under high pressure flows through the valve arrangement 140 into the outflow chamber 130. The spring arrangement 133 functions as a force producing device causing the diaphragm 132 to exert a preselected force on the fluid in the outflow chamber 130. This causes the valve 140 to open and close as the pressure in the outflow chamber 130 varies as fluid flows out of the outflow chambers 130 to the patient. This produces a steady, pressure regulated, flow of fluid from the storage chamber 120 into the outflow chamber 130, and from the outflow chamber 130 through the catheter assembly 170 to the patient. When the pressure of the fluid in the outflow chamber 130 reaches the preselected pressure (i.e., above 6.0 psi) the valve arrangement 140 closes blocking any further flow of fluid into the outflow chamber 130. When the pressure of the fluid in the outflow chamber 130 drops below the preselected pressure (i.e., below 6.0 psi) the valve arrangement 140 opens and allows higher pressure fluid from the storage chambers 120 to flow into the outflow chamber 130 bringing the pressure back up to the desired set point.

In the preferred embodiment the pressure of the drug in the outflow chamber is maintained at 6.0 psi ±5% with an outflow rate up to about 20 ml/hr depending on the number of catheter assemblies attached and the internal diameter and length of the flow restrictor 160 portion of delivery catheters attached to the pump. The pressure in the outflow chamber 130 is preselected by adjusting the set screw 134 which compresses spring 133. Fluid flows from the outflow chamber 130 at a constant pressure (i.e. 6.0 psi) through the catheter assembly or assemblies 170 to the patient. In the preferred embodiment shown, the catheter is attached to the infusion pump using a needle 60, the needle being inserted through an elastomeric septum 112.

While silicone polymer is a preferred material for the diaphragm 132 and the bladder 123 constituting the storage chambers 120, as well as the washer 136, which aids in sealing the one way valve, other elastomeric materials may be used such as polyisoprene or polyurethanes.

Other components which may be incorporated in the infusion device are a 5μ hydrophilic fluid filter 138 placed between the storage chamber 120 and the valve arrangement 140, and an air vent filter 142, preferably a 0.45μ hydrophobic filter, in the outflow chamber 130. As shown in FIG. 2, a pin or hollow rod 144 is enclosed within the bladders 123 to eliminate residual volume when the storage chamber 120 has emptied and the bladders 123 have fully collapsed. A piece of double-stick foam 152 is placed on the upper surface of the infusion pump 110 and over the adjustment screw 134 for use in retaining the catheter assembly 170 in place. The top of the infusion pump is enclosed by the removable cover 146 which protects the catheter 170 from damage or removal during use. In the embodiment shown the shape of the cover is designed to gently trap the catheter 170 against the upper adhesive face of the foam tape 152 without constricting flow through the catheter. The cover 146 is held in place by sealing cap 148 which twists on to close the feed opening of the one way fill valve 150 while at the same time contacting the outer surface of the cover, holding it in place.

It is evident from the foregoing that there are many additional embodiments of the present invention which, while not expressly described herein, are within the scope of this invention and may suggest themselves to one of ordinary skill in the art. For example, while FIG. 2 shows two separate bladders 123 mounted in parallel, a single bladder or multiple bladders may be utilized. By using multiple bladders one can flatten the infusion device profile (the thickness of the infusion pump), resulting in a device which can be readily shaped to sit closely against a users body for inconspicuous wearing. Multiple bladders also allow the quantity of fluid to be delivered to be increased without significantly increasing the thickness of the infusion device. Still further, while elastomeric bladders are disclosed for use in the drug delivery unit, any expandable chamber can be used. Therefore, a non-elastic but expandable bag or a bellows type container with an external pressure delivery means such as springs or pneumatics could also be used to pressurize of the chambers. In addition, pneumatic, or other means of providing a controlled pressure, such as a elastomeric material under a controlled compression, can be used in place of the spring controlling movement of the valve between the storage and outflow chambers. It is therefore intended that the invention be limited solely by the appended claims.

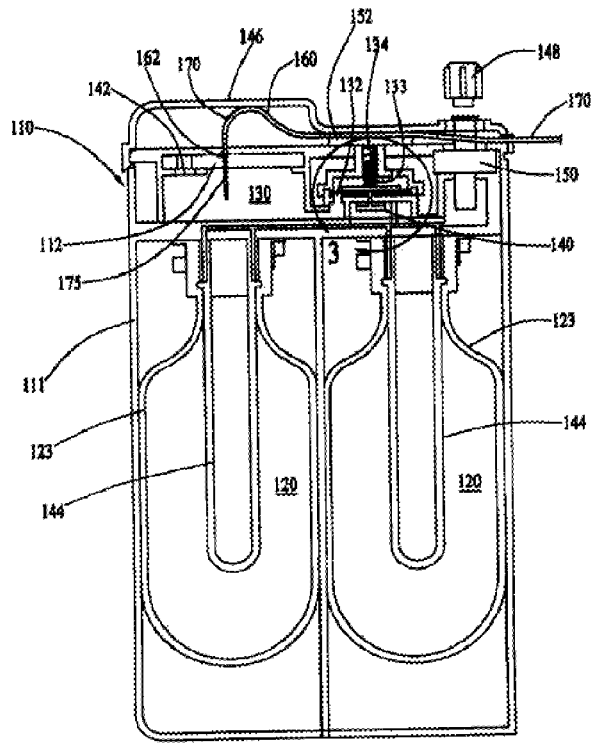

What is claimed is:

1. An infusion device for continuous delivery of a quantity of fluid into a living body at a substantially constant flow-rate over an extended period of time, comprising:
   a variable volume storage chamber for holding the fluid, said storage chamber including means for allowing fluid to be added to the storage chamber,
   a pressurizing means for the storage chamber, said pressurizing means maintaining the pressure within the storage chamber above a preselected outflow pressure,
   an outflow chamber for receiving fluid from the storage chamber, said outflow chamber including means for attachment thereto of a flow restrictor means and catheter through which fluid in the outflow chamber is delivered to a patient, and
   a pressure responsive valve means located between the storage chamber and the outflow chamber, said pressure responsive valve means functioning to maintain the fluid in the outflow chamber at the preselected outflow pressure,
   said pressure responsive valve means providing for fluid transfer from the storage chamber to the outflow chamber at a flow rate substantially equal to or greater than the flow rate out of the outflow chamber so that there is a continuous, uninterrupted and controlled volume of flow from the outflow chamber through the flow restrictor means and catheter to the patient over said extended period of time,
   wherein said pressure responsive valve means comprises:
   a valve attached to a flexible diaphragm such that the pressure of the fluid in the outflow chamber acts on the diaphragm to close the valve to prevent flow of fluid from the storage chamber to the outflow chamber when the pressure in the outflow chamber is elevated to the preselected outflow pressure, and
   a force applying means attached to the flexible diaphragm such that the force applied acts to open the valve when the pressure in the outflow chamber is less than the preselected outflow pressure, thereby allowing fluid in the storage chamber to enter the outflow chamber and the pressure in the outflow chamber to be held at a substantially constant preselected outflow pressure.

2. The infusion device of claim 1 wherein the force applying means is a spring, pneumatic device, or compressed elastomeric material.

3. The infusion device of claim 1 wherein the preselected outflow pressure ranges from about 1 psi to about 10 psi with an accuracy of ±5%.

4. The infusion device of claim 1 wherein the storage chamber has a volume ranging from 50 ml to 500 ml and the outflow chamber has volume ranging from 2 ml to 10 ml.

5. The infusion device of claim 1 wherein the pressurizing means for the storage chamber comprises an elastomeric bladder, springs, or a pneumatic system.

6. An infusion device for continuous delivery of a quantity of fluid into a living body at a substantially constant flow-rate over an extended period of time, comprising:
   a variable volume storage chamber for holding the fluid, said storage chamber including means for allowing fluid to be added to the storage chamber,
   a pressurizing means for the storage chamber, said pressurizing means maintaining the pressure within the storage chamber above a preselected outflow pressure,
   an outflow chamber for receiving fluid from the storage chamber, said outflow chamber including means for attachment thereto of a flow restrictor means and catheter through which fluid in the outflow chamber is delivered to a patient, and
   a pressure regulator means located between the storage chamber and the outflow chamber, said pressure regulator means functioning to maintain the fluid in the outflow chamber at the preselected outflow pressure,
   said pressure regulator means providing for fluid transfer from the storage chamber to the outflow chamber at a flow rate substantially equal to or greater than the flow rate out of the outflow chamber so that there is a continuous, uninterrupted and controlled volume of flow from the outflow chamber through the flow restrictor means and catheter to the patient over said extended period of time
wherein the storage chamber comprises multiple bladders.

7. An infusion device for delivering a quantity of fluid into a living body at a substantially constant flow-rate over an extended period of time, comprising:
  a first chamber for storing a volume of the fluid,
  a second chamber operatively attached to the first chamber for receiving fluid from the first chamber,
  a regulator means located between the first chamber and the second chamber, said regulator means functioning to maintain the pressure in the second chamber at a preselected outflow pressure while providing fluid transfer from the first chamber to the second chamber at a rate substantially equal to or greater than said substantial constant flow-rate into the living body from the second chamber,
  and a pressurizing means for maintaining the pressure within the first chamber above the preselected outflow pressure,
  said first chamber including fluid input means and said second chamber including means for attachment thereto of a fluid delivery tube, said fluid delivery tube including flow restrictor means through which fluid in the second chamber is delivered to a patient in an uninterrupted manner over an extended period of time and wherein the first chamber comprises multiple storage containers.

* * * * *

UNITED STATES PATENT AND TRADEMARK OFFICE
CERTIFICATE OF CORRECTION

| | | |
|---|---|---|
| PATENT NO. | : 7,022,107 B1 | |
| APPLICATION NO. | : 09/670735 | |
| DATED | : April 4, 2006 | |
| INVENTOR(S) | : James Christensen et al. | |

It is certified that error appears in the above-identified patent and that said Letters Patent is hereby corrected as shown below:

The Title Page, showing an illustrative figure, should be deleted and substitute therefor the attached title page.

Replace Figure 1 with the corrected Figure 1 as attached.

Signed and Sealed this

Eighth Day of July, 2008

JON W. DUDAS
*Director of the United States Patent and Trademark Office*

(12) United States Patent
Christensen et al.

(10) Patent No.: US 7,022,107 B1
(45) Date of Patent: Apr. 4, 2006

(54) INFUSION PUMP WITH PRESSURE REGULATOR

(75) Inventors: James Christensen, Glendora, CA (US); John Krug, Orange, CA (US)

(73) Assignee: Advanced Infusion, Inc., Tempe, AZ (US)

(*) Notice: Subject to any disclaimer, the term of this patent is extended or adjusted under 35 U.S.C. 154(b) by 0 days.

(21) Appl. No.: 09/670,735

(22) Filed: Sep. 27, 2000

Related U.S. Application Data

(63) Continuation-in-part of application No. 09/400,579, filed on Sep. 22, 1999.

(51) Int. Cl.
*A61M 37/00* (2006.01)
(52) U.S. Cl. .................... 604/141; 604/891.1
(58) Field of Classification Search ......... 604/890.1, 604/891.1, 151, 153, 154, 131, 132–135, 604/150, 152, 141, 892.1
See application file for complete search history.

(56) References Cited

U.S. PATENT DOCUMENTS

| | | | |
|---|---|---|---|
| 3,731,681 A | 5/1973 | Blackshear et al. | 128/214 |
| 3,993,069 A | 11/1976 | Buckles et al. | 128/214 F |
| 4,106,510 A | 8/1978 | Hakim et al. | 128/350 |
| 4,299,220 A | 11/1981 | Dorman | 128/260 |
| 4,714,462 A * | 12/1987 | DiDomenico | 604/67 |
| 4,718,893 A | 1/1988 | Dorman et al. | 604/67 |
| 4,772,263 A | 9/1988 | Dorman et al. | 604/132 |
| 5,061,242 A | 10/1991 | Sampson | 604/118 |
| 5,067,943 A | 11/1991 | Burke | 604/141 |
| 5,080,652 A | 1/1992 | Sancoff et al. | 604/132 |
| 5,088,983 A | 2/1992 | Burke | 604/141 |
| 5,242,406 A | 9/1993 | Gross et al. | 604/132 |

* cited by examiner

*Primary Examiner*—Kevin C. Simmons
(74) *Attorney, Agent, or Firm*—Koppel, Jacobs, Patrick & Heybl; Michael J. Ram

(57) ABSTRACT

An infusion pump for infusing drugs or other fluids into the body. The pump consists of two chambers. The storage chamber holds a large volume of drug at a variable and elevated pressure, which exceeds the preselected outflow pressure. The outflow chamber holds a smaller volume of drug at a constant outflow pressure. A moveable diaphragm attached to a valve controls the entry of the drug from the storage chamber into the outflow chamber. The pressure of the drug in the outflow chamber is determined by the forces applied to the diaphragm. The drug from the outflow chamber flows through a flow restrictor and catheter into the patient at a constant flow rate.

7 Claims, 3 Drawing Sheets